United States Patent
Salah et al.

(10) Patent No.: US 12,419,729 B2
(45) Date of Patent: *Sep. 23, 2025

(54) METHOD OF ANALYSIS OF A REPRESENTATION OF A DENTAL ARCH

(71) Applicant: DENTAL MONITORING, Paris (FR)

(72) Inventors: Philippe Salah, Paris (FR); Thomas Pellissard, Clichy (FR)

(73) Assignee: DENTAL MONITORING, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 18/615,239

(22) Filed: Mar. 25, 2024

(65) Prior Publication Data

US 2024/0261076 A1  Aug. 8, 2024

Related U.S. Application Data

(63) Continuation of application No. 16/965,539, filed as application No. PCT/EP2019/052127 on Jan. 29, 2019, now Pat. No. 11,963,840.

(30) Foreign Application Priority Data

Jan. 30, 2018  (EP) ..................... 18154284

(51) Int. Cl.
*A61C 19/00* (2006.01)
*A61C 7/00* (2006.01)
(Continued)

(52) U.S. Cl.
CPC .............. *A61C 19/04* (2013.01); *A61C 7/002* (2013.01); *G16H 30/40* (2018.01); *G16H 50/20* (2018.01); *G16H 50/70* (2018.01)

(58) Field of Classification Search
CPC ..... A61C 19/04; A61C 7/002; A61C 382/128; G16H 50/70; G16H 50/20; G16H 30/40
See application file for complete search history.

(56) References Cited

U.S. PATENT DOCUMENTS

2002/0150859 A1 * 10/2002 Imgrund ................ A61C 7/00
433/24
2007/0129991 A1 * 6/2007 Kuo ....................... B33Y 80/00
705/2

(Continued)

FOREIGN PATENT DOCUMENTS

EP        3050534 A1 *  8/2016 ........... A61B 5/0035
EP        4129231 A1 *  2/2023 ........... A61B 5/7275

*Primary Examiner* — Khai M Nguyen
(74) *Attorney, Agent, or Firm* — Ronald M. Kachmarik; Cooper Legal Group LLC

(57) ABSTRACT

Method of analysis of a diagnostic dental representation showing a dental arch of a current patient in several dimensions. The method includes creation of a learning base including more than 1,000 historical dental structures. Each historical dental structure includes a historical dental representation showing an arch of a historical patient in several dimensions and a historical specification containing a value for at least a first attribute relating to a dental object associated with the historical dental representation. The method includes training of at least one deep learning device by use of the learning base. The method includes submission of the diagnostic dental representation to the deep learning device in such a manner that it determines, for the diagnostic dental representation, at least one value for the first attribute.

14 Claims, 1 Drawing Sheet

1) creation of a learning base consisting of enriched dental representations 2) training of a deep learning device with the learning base 3) submission of the diagnostic dental representation to the learning device

(51) Int. Cl.
*A61C 19/04* (2006.01)
*G16H 30/40* (2018.01)
*G16H 50/20* (2018.01)
*G16H 50/70* (2018.01)

(56) References Cited

U.S. PATENT DOCUMENTS

| | | | |
|---|---|---|---|
| 2008/0124681 A1* | 5/2008 | Cha | A61C 9/0053 703/7 |
| 2014/0324919 A1* | 10/2014 | Badawi | G06F 30/20 707/803 |
| 2014/0329194 A1* | 11/2014 | Sachdeva | A61C 7/002 433/24 |
| 2016/0051348 A1* | 2/2016 | Boerjes | A61C 11/08 433/215 |
| 2016/0055312 A1* | 2/2016 | Badawi | G16H 30/40 703/11 |
| 2019/0255778 A1* | 8/2019 | Lucas | G05B 19/4099 |

* cited by examiner 1) creation of a learning base consisting of enriched dental representations 2) training of a deep learning device with the learning base 3) submission of the diagnostic dental representation to the learning device

METHOD OF ANALYSIS OF A REPRESENTATION OF A DENTAL ARCH

TECHNICAL FIELD

The present invention relates to the field of the analysis of representations of dental arches.

PRIOR ART

Optical or "3D" scanners allow three-dimensional models of the surfaces of the mouth to be created, but do not allow information on the non-visible parts of the mouth to be acquired. The non-visible parts of the mouth comprise, in particular, embedded teeth, roots of teeth and the maxillary and mandibular bones.

In order to acquire such information, a tomographic acquisition is conventionally carried out, preferably by cone-beam computed tomography, or CBCT. An acquisition by means of a conventional X-ray apparatus is also possible but does not always provide a sufficient resolution.

The application of X-rays may be detrimental to health, in particular if it is repeated. It is not therefore practiced for preventive purposes. In other words, the non-visible parts of the mouth are generally only analyzed when the patient complains of pain or observes abnormal phenomena such as teeth that are too "mobile".

The diagnosis is therefore late and the treatment long and complex.

There accordingly exists a need for a method allowing the position and/or the shape of non-visible parts of the mouth to be evaluated and which does not pose the aforementioned problems.

Furthermore, everyone has an interest in predicting future changes to their dental system, in other words not only to the visible teeth but also to the embedded teeth, to the jaws or to the periodontium. Only examining the visible parts of the mouth does not allow such changes to be predicted with precision.

There accordingly also exists a need for a method allowing future changes to the dental system to be anticipated, independently of any diagnosis.

Lastly, the orthodontist only having limited information on the configuration of the dental system of the patient may be led to carry out unnecessary or detrimental procedures. For example, he/she may require the patient to wear an orthodontic appliance in order to modify the position of a tooth which, in the absence of any treatment, would have naturally moved toward this position.

There accordingly exists an ongoing need to enrich the information made available to the orthodontist.

One aim of the invention is to, at least partially, satisfy these needs.

SUMMARY OF THE INVENTION

The invention provides a method of analysis of a dental representation of a dental arch of a patient, referred to as "diagnostic dental representation", in which method the diagnostic dental representation is submitted to a deep learning device, preferably a neural network, in order to determine at least one piece of dental information relating to a dental object associated with the diagnostic dental representation and chosen from between:
  a visible part of the arch, notably a crown or a set of crowns, or a visible arch; or
  a non-visible part of said arch, notably a root or a set of roots or one or more embedded teeth.

The term "non-visible part" is understood to mean a part of the arch which may not be seen in visible light, notably with the naked eye and, in particular, without the use of X-rays.

The dental representation may in particular, be an image or a group of images relating to the dental arch of the patient.

A dental object is said to be "associated" with a dental representation when this dental object is shown in the dental representation, for example a crown, or when it is linked to an element shown in the dental representation, for example a root, generally not visible, of a crown.

The invention provides, in particular, a method of analysis of a diagnostic dental representation showing a dental arch of a current patient in several dimensions, said method comprising the following steps:
  1) creation of a learning base comprising more than 1,000 historical dental structures, each historical dental structure comprising:
     a historical dental representation showing an arch of a historical patient in several dimensions, and
     a historical specification containing a value for at least a first attribute relating to a dental object associated with said historical dental representation,
  2) training of at least one deep learning device, preferably a neural network, by means of the learning base;
  3) submission of the diagnostic dental representation to the deep learning device in such a manner that it determines, for said diagnostic dental representation, at least one value for said first attribute.

As will be seen in more detail in the following part of the description, a method of analysis according to the invention advantageously allows dental information contained in the diagnostic dental representation to be immediately recognized, but that an orthodontist would have difficulties in identifying or could not identify. Its implementation thus contributes to the quality of the treatment.

In one embodiment, at the step 3), not only the diagnostic dental representation, but also an analysis specification containing a value for at least a second attribute for which the historical specifications provide a value are submitted to the deep learning device. The precision of this analysis is accordingly considerably improved.

The dependent claims provide preferred features of a method according to the invention.

The invention relates, in particular, to the use of a method according to the invention for monitoring the position and/or of the shape of a non-visible part of the mouth and, in particular, roots of the teeth.

The invention lastly relates to:
  a computer program and, in particular, a specialized application for mobile telephones, comprising program code instructions for the execution of one or more steps of a method according to the invention, when said program is executed by a computer,
  a data medium on which such a program is recorded, for example a memory or a CD-ROM.

Definitions

A dental representation of an arch is a digital model in several dimensions representing all or part of said arch. The dental representation may notably be an image in two dimensions, a group of images relating to the same arch, a digital three-dimensional model or a hologram.

An "image" is understood to mean an image in two dimensions, such as a photograph or an image extracted from a film. An image is formed of pixels.

The group of images may comprise several images acquired at the same time and constituting for example a representation in several sections of the dental arch. The group of images may also comprise several images acquired at different times, for example separated by more than a week or more than a month. The representation is thus composed of a sequence of images and provides temporal information on the dental arch. It may be referred to as a "dynamic representation", or as a "representation in four dimensions" of the arch.

The term "specification" of a dental representation is understood to mean a set of values for attributes of this dental representation.

A dental representation and a specification of this dental representation together constitute a "dental structure", or "enriched dental representation".

A dental representation, and in particular an image or a group of images, is said to be "historical" when it has been acquired in the past. A dental structure is said to be "historical" when it refers to a historical dental representation. The historical dental structures are placed in the learning base in order to train the deep learning device.

Each dental representation may be characterized by a specification supplying a set of values, specific to this dental representation, for a set of attributes. The number of possible values for an attribute is not limited.

A deep learning device is capable of evaluating attribute values of a dental representation submitted to it, in other words of a diagnostic dental representation. For this purpose, it must first of all learn to analyze the dental representations. A learning base is therefore submitted to it consisting of a large number of historical dental structures, each composed of a historical dental representation and of a historical specification supplying the values of the attributes for the historical dental representation, said values being established, for example manually, based on the knowledge of those skilled in the art.

In order for the deep learning device to be able to evaluate the value of an attribute of the diagnostic dental representation, the historical dental structures must of course supply values for this attribute or for equivalent attributes.

A "patient" is a person for which a dental representation has been acquired, independently of the fact that this person is undergoing an orthodontic treatment or not. The method distinguishes the "current" patient, from whom the diagnostic dental representation is acquired, and the historical patients, from whom the historical dental representations of the learning base are acquired.

An "orthodontist" is understood to mean any person qualified to administer dental treatment, which also includes a dentist.

An "orthodontic component" is understood to mean all or part of an orthodontic appliance.

An orthodontic component may in particular, be an orthodontic aligner. Such an aligner extends in such a manner as to follow the successive teeth of the arch onto which it is fixed. It defines a trough with a general U-shape, whose shape is determined to ensure the fixing of the aligner onto the teeth, but also according to a desired target positioning for the teeth. More precisely, the shape is determined in such a manner that, when the aligner is in its operating position, it exerts forces tending to displace the teeth under treatment toward their target positioning, or to maintain the teeth in this target positioning.

The "operating position" is the position in which the orthodontic component is worn by the patient.

The "calibration" of an acquisition apparatus consists of the set of values of the calibration parameters. A "calibration parameter" is a parameter intrinsic to the acquisition apparatus (as opposed to its position and its orientation) whose value influences the image acquired. Preferably, the calibration parameters are chosen from within the group formed by the lens aperture, the exposure time, the focal distance and the sensitivity.

The terms "comprising" or "exhibiting" or "having" should be interpreted in a non-restrictive manner, unless indicated otherwise.

BRIEF DESCRIPTION OF THE FIGURES

Other features and advantages of the invention will become more clearly apparent upon reading the detailed description that follows and upon examining the appended drawing in which FIG. 1 shows, schematically, the various steps of a method of analysis according to the invention.

DETAILED DESCRIPTION

At step 1), a set of historical dental representations is collected in order to create the learning base.

Preferably, this set comprises more than 1,000, more than 5,000, more than 10,000, preferably more than 30,000, preferably more than 50,000, preferably more than 100,000 dental representations.

Each historical dental representation is analyzed, conventionally by an operator, in order to establish the historical specification for this dental representation.

In particular, for each dental representation collected, an operator may identify the areas showing a crown, the numbers of teeth and/or the associated pathologies, the areas showing an orthodontic component and any associated defects, for example a potential detachment of the aligners/braces. It thus assigns attribute values to the attributes of the dental representation.

For example, upon examining a historical dental representation comprising the representation of an aligner in operation, for example an image, an orthodontist is able to determine the value of the attribute "positioning of the aligner", in other words to establish whether this value must be "aligner correctly positioned" or "aligner incorrectly positioned". This value may thus form part of the historical specification of the historical dental representation.

Attribute

An attribute may relate to a dental object, in other words an object relating to the manducation system. For example, an attribute may relate to the position and/or to the nature of a crown, of a root, of an alveolar bone, of an arch, of the tongue, of the mouth, of the lips, of a jaw, of the gum, of the overall manducation system or of an orthodontic component worn by the patient.

For example, it may identify the areas of teeth in the dental representation, the position of the tongue (for example "retracted") or the opening of the mouth of the patient (for example "mouth open" or "mouth closed") or the general dental situation (for example "dental situation satisfactory" or "dental situation unsatisfactory"), or the presence of a representation of an orthodontic appliance and/or its state (for example appliance "intact", "broken" or "damaged"), or information on the patient (for example the age of the patient or relating to their environment or to their habits, notably eating habits, or on the treatment that they are receiving or that they have received in the past).

A tooth attribute is preferably chosen from amongst the number of a tooth, a type of tooth, whose possible values would for example be "incisor", "canine" or "molar", a shape parameter for the tooth, for example the width of a tooth, in particular a mesio-palatal width, a thickness, a crown height, an index of mesial and distal deflection of the incisal edge, or a level of abrasion, an appearance parameter for the tooth, in particular a translucidity index or a color parameter, a parameter relating to the state of the tooth, for example "abraded", "broken", "decayed" or "fitted" (in other words in contact with an orthodontic appliance), or a combination of these attributes. A tooth attribute may also be its translational speed or rotational speed about an axis in space. In one embodiment, attributes of teeth supply values for the translational speeds along at least three axes forming a reference frame in space and for the rotational speeds around at least three axes forming a reference frame in space.

In one particularly advantageous embodiment, the first attribute relates to a dental object not shown on the dental representation in question. In particular, the first attribute may relate to a hidden part of the tooth, for example relating to the root of the tooth.

For a group of images, attributes may be global attributes for the group, for example when they relate to the general dental situation. Attributes may be specific to each image, such as the time of acquisition of the image. Attributes may lastly, be specific to parts of each image, such as the position of the areas of teeth shown.

Group attributes may in particular relate to the speed of displacement of a visible part of the mouth and, in particular, of teeth, or relate to the treatment in the course of which the images of the group have been acquired.

An attribute may also relate to an object other than a dental object, for example on the acquisition apparatus of the dental representation in question. For example, for an image, an attribute may relate to a position and/or an orientation and/or a calibration of an acquisition apparatus used to acquire said image, for example a mobile telephone or a 3D scanner. It may for example take the values "face on photo", "photo from left" and "photo from right".

An attribute may also relate to a property of the dental representation, for example, it may relate to an identifier of the images from a group, or, for an image, relate to the date of acquisition of the image, to the group to which the image belongs, to the brightness, to the contrast or to the sharpness of the image. It may for example take the values "insufficient contrast" and "acceptable contrast".

The attributes may also be classified depending on whether they relate to only a part of a dental representation, or "specific attribute", or the dental representation as a whole, "global attribute".

For example, a global attribute may relate to the acquisition apparatus used for the acquisition of the dental representation or to the context of this acquisition. A specific attribute may relate to a tooth shown, or "tooth attribute".

At least one attribute relates to a dental object. The first attribute may notably be any one of the attributes described hereinabove relating to a dental object.

In one preferred embodiment, the determination of the historical specifications is, at least in part, automatic.

Preferably, the value of at least one attribute of a first historical dental representation is determined by means of values of one or more attributes of one or more historical dental representations acquired previously. For example, if two dental representations relate to the same patient, the age of the patient input into the attribute "age" of the prior dental representation allows the age of the patient to be deduced from the first dental representation, taking into account the time difference between the times of acquisition of the two historical dental representations.

In one embodiment, in order to describe a historical dental representation of a dental arch of a patient, a deformation is applied to an initial three-dimensional physical model of said arch in such a manner as to obtain a deformed three-dimensional physical model exhibiting a maximum match with said historical dental representation. The initial three-dimensional physical model may in particular, be a 3D optical scan, for example carried out at the start of the treatment. The acquisition of the historical dental representation may for example be more than a week, a month, or two months after the generation of the initial three-dimensional physical model.

A "match" (or "fit") between two objects is a measure of the difference between these two objects. A match is maximum ("best match" or "best fit") when it results from an optimization allowing said difference to be minimized.

A deformed three-dimensional physical model exhibits a best match with a historical dental representation when this model has been chosen from amongst several models since it allows an observation, for example a view, exhibiting a maximum match with said historical dental representation, for example an image.

The search for the optimum deformation, in other words resulting in the deformed three-dimensional physical model exhibiting a maximum match with said historical dental representation, is preferably performed via first and second operations.

During the first operation, an observation, or "view", of the model exhibiting a maximum match with the dental representation is sought.

During the second operation, optional but preferred, an additional deformation of the model is sought, then the first operation is repeated. The two operations are repeated until a deformed three-dimensional physical model exhibiting a maximum match with said historical dental representation is obtained.

Preferably, the first operation and/or the second operation, preferably the first operation and the second operation, implement a metaheuristic method, preferably evolutionist, preferably a simulated annealing.

The metaheuristic method is preferably chosen from within the group formed by
 evolutionary algorithms, preferably chosen from amongst: evolutionary strategies, genetic algorithms, differential evolution algorithms, distribution estimation algorithms, artificial immunity systems, the Shuffled Complex Evolution path re-composition, simulated annealing, ant colony algorithms, particle swarm optimization algorithms, taboo search, and the GRASP method;
 the kangaroo algorithm,
 the method of Fletcher and Powell,
 the sound-effects method,
 stochastic tunneling,
 hill climbing with random restarts,
 the cross-entropy method, and
 hybrid methods between the aforementioned metaheuristic methods.

Certain attribute values of the initial three-dimensional physical model are identical in the deformed three-dimensional physical model, and may therefore be automatically attributed to the dental representation. For example, if the teeth are modeled in the initial three-dimensional physical model (segmentation of the model) and if the deformation is a displacement of one or more models of teeth, the models of teeth are identifiable in the deformed three-dimensional physical model, but also, as a consequence, on the historical dental representation. The deformed three-dimensional physical model has indeed been determined so that the historical dental representation may be observed on it. The tooth areas identified on the initial three-dimensional physical model may also be automatically identified on the historical dental representation.

Advantageously, the deformation of the three-dimensional physical model is possible when the historical dental representation is a photograph or a film taken without any particular precaution, for example with a mobile telephone, such as described in WO 2016 066651.

At step 2), one or more deep learning devices are trained by means of the learning base.

A deep learning device is preferably a neural network. A neural network or "artificial neural network" is a set of algorithms well known to those skilled in the art.

The neural network may in particular, be chosen from amongst:
  the networks specialized in the classification of images, called "CNN" ("Convolutional neural network"), for example
    AlexNet (2012)
    ZF Net (2013)
    VGG Net (2014)
    GoogleNet (2015)
    Microsoft ResNet (2015)
    Caffe: BAIR Reference CaffeNet, BAIR AlexNet
    Torch: VGG_CNN_S,VGG_CNN_M, VGG_CNN_M_2048,VGG_CNN_M_1024, VGG_CNN_M_128,VGG_CNN_F,VGG ILSVRC-2014 16-layer,VGG ILSVRC-2014 19-layer, Network-in-Network (Imagenet & CIFAR-10)
    Google: Inception (V3, V4).
  the networks specialized in the localization and detection of objects in an image, the Object Detection Network, for example:
    R-CNN (2013)
    SSD (Single Shot MultiBox Detector: Object Detection network), Faster R-CNN (Faster Region-based Convolutional Network method: Object Detection network)
    Faster R-CNN (2015)
    SSD (2015).

The list hereinabove is not limiting.

Training a deep learning device in the form of a neural network conventionally consists in activating the neurons composing it. The interconnection of these neurons then defines the architecture of the network. More precisely, the values of the parameters are sought which, when the historical dental representations of the learning base are submitted to the deep learning device parameterized with said values, allow it to determine attribute values which come as close as possible to the attribute values of the historical specifications associated with said historical dental representations.

The training allows the deep learning device to progressively learn to recognize patterns on a dental representation and to associate them with attribute values.

After having been trained with the learning base, the deep learning device can thus determine values for the attributes of a diagnostic dental representation, without intervention of those skilled in the art.

At step 3), the diagnostic dental representation of the current patient is submitted to the deep learning device. The deep learning device accordingly determines at least one value for the first attribute relating to the dental object. It thus enriches the specification for analyzing the diagnostic dental representation. Preferably, the deep learning device determines probabilities for the various possible values for said first attribute.

In one embodiment, based on the attribute value or values supplied by the deep learning device for the first attribute, dental information relating to said dental object is further determined, then this dental information is transmitted to an operator.

The dental information may, in particular, comprise a value for the first attribute of the diagnostic dental representation or a probability relating to such a value.

The dental information generated by the method of analysis may be derived from one or more attribute values. For example, it may relate to the dental situation of the patient and, in particular, to a risk of occurrence of a pathological situation, relating to a visible part of the mouth, for example a risk of malocclusion, or to a non-visible part of the mouth, for example relating to a risk of rhizalyse.

For example, if an attribute of the historical dental representations globally defines, for each historical dental representation taken as a whole, whether a dental situation "is pathological" or "is not pathological", the dental information generated by the method of analysis may be a value of this attribute for the diagnostic dental representation. Alternatively, this dental information may be deduced from other values of equivalent attributes, for example from a tooth attribute value indicating that a tooth "is decayed".

The invention is particularly useful for the evaluation of the position and/or of the shape of a non-visible part of the manducation system, and notably of roots of teeth or of embedded teeth.

For example, in order to monitor the rhizalyse, a learning base is constructed using historical dental representations, for example photos, on which an orthodontist identifies the teeth having suffered a rhizalyse, and informs the historical specification accordingly.

It goes without saying that, in order to identify these teeth on a historical dental representation, for example on an image, the orthodontist may have used means other than the image alone. In particular, he/she may have used information acquired prior to and/or after the acquisition of said image, for example more than 1 week, 1 month or one year before or after the acquisition of the historical dental representation. In particular, he/she may have learned that the image corresponded to a risk of rhizalyse when the rhizalyse occurred.

He/she may also have used images acquired by X-rays, for example by conical-beam computed tomography.

In one embodiment, the learning base comprises groups of images, acquired at different times for the same patient. The historical specification of a group may indicate, for each image, the tooth or teeth having suffered a rhizalyse, together with the date of acquisition of the image and/or the speeds of displacement of the teeth. The deep learning device is then capable of integrating not only the influence of the arrangement of the teeth on the risk of rhizalyse, but also the speed of displacement of the teeth.

The knowledge of the changes to the dental situation over time considerably improves the results obtained with a method according to the invention.

For example, a dental situation, which upon examining a single diagnostic image appeared as "non-pathological", might be considered as "potentially pathological" when the analysis of the group of diagnostic images demonstrates a change over time which, with regard to the learning base, must be considered as potentially pathological.

Furthermore, certain dental situations can only be correctly evaluated by analyzing a group of diagnostic images allowing several regions of the mouth to be observed simultaneously that a single image would not allow to be visualized. The group of diagnostic images may also comprise diagnostic images acquired at different times.

Generally speaking, the use of groups of images as dental representations advantageously allows the quantity of information available to be increased.

EXAMPLE

In one preferred embodiment, the historical dental structures of the learning base each comprise an image acquired by conical-beam computed tomography and a historical specification indicating the treatment in the framework of which said image has been acquired, the identification of the types of tooth shown on said image (for example "canines", "molars", etc.), the speeds of displacement of these teeth and information on the occurrence of a rhizalyse in the framework of this treatment.

The attributes are thus, for example,
the nature of the treatment undertaken;
for each tooth shown:
  the type of tooth;
  the translational speed along the axis Ox), in a reference frame of the space Oxyz),
  the translational speed along the axis Oy),
  the translational speed along the axis Oz),
  the rotational speed around the axis Ox),
  the rotational speed around the axis Oy),
  the rotational speed around the axis Oz),
  occurrence of a rhizalyse in the framework of this treatment?

The speeds of displacement may in particular have been evaluated by analyzing images acquired by means of a conventional scanner.

The image acquired by conical-beam computed tomography is preferably an image acquired at the start of a course of treatment.

After having trained a deep learning device, preferably a neural network, with this learning base, the diagnostic dental representation of a patient, namely an image acquired by conical-beam computed tomography, is submitted to it preferably at the beginning of the treatment.

Preferably, the incomplete analysis specification for the diagnostic dental representation is also submitted to it. Preferably, the analysis specification comprises attribute values for at least the attributes whose values constitute the historical specifications of the historical dental structures, except for the attribute "occurrence of a rhizalyse in the framework of this treatment?". In other words, it is indicated to the deep learning device what are the values for the following attributes of the diagnostic dental representation:
treatment undertaken;
for each tooth shown:
  type of tooth;
  translational speed along the axis Ox), in a reference frame of the space Oxyz),
  translational speed along the axis Oy),
  translational speed along the axis Oz),
  the rotational speed around the axis Ox),
  the rotational speed around the axis Oy),
  the rotational speed around the axis Oz).

The first attribute is therefore "occurrence of a rhizalyse in the framework of this treatment?".

Using this set of information, the deep learning device supplies a probability for each of the possible values of the first attribute, in other words a probability of the value being "yes" and a probability of the value being "no".

It is thus possible to determine a probability of occurrence of the rhizalyse without having to acquire a new image by conical-beam computed tomography.

The evaluation of a risk of rhizalyse does not constitute a diagnosis. It does however allow situations with a significant risk to be detected. In order to establish a diagnosis, it is still necessary to carry out a tomographic acquisition. The invention however allows such tomographic acquisitions to be considerably limited by detecting the situations with a significant risk.

The invention also enables an early pre-diagnosis, and thus the occurrence of a rhizalyse to be anticipated.

Advantageously, this pre-diagnosis is easy to implement and may be generalized.

Lastly, as has now become clearly apparent, the invention allows the orthodontist to benefit from a more detailed knowledge of the dental situation of their patient, which limits the risk of them performing unnecessary or detrimental acts.

It goes without saying that the invention is not limited to the embodiments described hereinabove and shown.

In particular, the patient is not limited to a human being. A method according to the invention may be used for another animal.

The invention claimed is:

1. A non-transitory computer medium storing computer-program instructions for executing a method of analysis of a diagnostic dental representation showing a dental arch of a current patient in several dimensions, said method comprising the following step:
submission of the diagnostic dental representation to a deep learning device trained by means of a learning base, in such a manner that it determines, for said diagnostic dental representation, at least one value for a first attribute related to a dental object not shown on the dental representation, the learning base comprising more than 1,000 historical dental structures, each historical dental structure comprising:
  a historical dental representation showing an arch of a historical patient in several dimensions, and
  a historical specification containing a value for at least said first attribute relating to a dental object associated with said historical dental representation.

2. The non-transitory computer medium according to claim 1, in which, not only the diagnostic dental representation, but also an analysis specification containing a value for at least a second attribute for which each historical specification supplies a value are submitted to the deep learning device.

3. The non-transitory computer medium according to claim 2, in which the analysis specification contains a value for at least the following second attributes:
  treatment in progress;

for each tooth shown on the diagnostic dental representation:
type of tooth;
translational speed along one or more axes and/or rotational speed around one or more axes.

4. The non-transitory computer medium according to claim 1, in which the first attribute relates to the occurrence of a rhizalyse.

5. The non-transitory computer medium according to claim 1, in which the diagnostic dental representation and the historical dental representations show, in at least three dimensions, said dental arch.

6. The non-transitory computer medium according to claim 1, in which the diagnostic dental representation and the historical dental representations
are all groups of images, or
are all three-dimensional digital models, or
are all holograms.

7. The non-transitory computer medium according to claim 1, in which the diagnostic dental representation and the historical dental representations comprise groups of images acquired simultaneously, or acquired successively, at least two of said images acquired successively having been acquired at more than a one month interval.

8. The non-transitory computer medium according to claim 1, in which the dental object is not visible.

9. The non-transitory computer medium according to claim 8, in which the non-visible dental object is a root of a tooth or an embedded tooth.

10. The non-transitory computer medium according to claim 1, in which said first attribute relates to
a part, visible or non-visible, of the dental arch shown on each historical dental representation,
a position and/or an orientation and/or a calibration of an acquisition apparatus used to acquire said historical dental representation, and/or
a property of the historical dental representation and, in particular, relating to the brightness, to the contrast or to the sharpness of the historical dental representation.

11. The non-transitory computer medium according to claim 1, in which at least one value of an attribute of a first historical dental representation is determined by means of values of one or more attributes of one or more historical dental representations acquired at an earlier or later date.

12. The non-transitory computer medium according to claim 11, in which at least one value of an attribute of a historical dental representation is determined by means of values of one or more attributes of a deformed three-dimensional physical model resulting from a deformation of an initial three-dimensional physical model generated by means of an optical scanner.

13. The non-transitory computer medium according to claim 12, in which said deformation is determined so that the deformed three-dimensional physical model exhibits a best match with the historical dental representation.

14. The non-transitory computer medium according to claim 13, in which said best match is sought
i) by searching for an observation of a three-dimensional physical model to be tested, initially chosen as the initial three-dimensional physical model, which exhibits the best match with the historical dental representation, then
ii) by deforming the three-dimensional physical model to be tested, then re-starting from the step i) until a three-dimensional physical model to be tested is obtained allowing an observation which exhibits a best match with the historical dental representation.

* * * * *